(12) United States Patent
Yavari et al.

(10) Patent No.: US 10,864,008 B2
(45) Date of Patent: Dec. 15, 2020

(54) CURVED RESECTOSCOPE

(71) Applicants: Parviz Yavari, Huntington Park, CA (US); Morteza Yavari, Jacksonville, FL (US)

(72) Inventors: Parviz Yavari, Huntington Park, CA (US); Morteza Yavari, Jacksonville, FL (US)

( * ) Notice: Subject to any disclaimer, the term of this patent is extended or adjusted under 35 U.S.C. 154(b) by 297 days.

(21) Appl. No.: 16/027,038

(22) Filed: Jul. 3, 2018

(65) Prior Publication Data

US 2019/0150971 A1    May 23, 2019

Related U.S. Application Data

(60) Provisional application No. 62/707,821, filed on Nov. 20, 2017.

(51) Int. Cl.

| | | |
|---|---|---|
| *A61B 18/12* | (2006.01) | |
| *A61B 17/32* | (2006.01) | |
| *A61B 18/14* | (2006.01) | |
| *A61B 18/00* | (2006.01) | |
| *A61B 90/00* | (2016.01) | |

(52) U.S. Cl.
CPC ...... *A61B 17/320016* (2013.01); *A61B 18/14* (2013.01); *A61B 18/149* (2013.01); *A61B 2018/00517* (2013.01); *A61B 2018/00547* (2013.01); *A61B 2018/00601* (2013.01); *A61B 2018/1407* (2013.01); *A61B 2090/3614* (2016.02); *A61B 2217/005* (2013.01); *A61B 2217/007* (2013.01); *A61B 2218/002* (2013.01); *A61B 2218/007* (2013.01)

(58) Field of Classification Search
CPC .................................................. A61B 18/149
See application file for complete search history.

(56) References Cited

U.S. PATENT DOCUMENTS

| | | | | |
|---|---|---|---|---|
| 4,976,697 | A * | 12/1990 | Walder | A61M 25/0017 604/164.02 |
| 5,669,906 | A * | 9/1997 | Grossi | A61B 18/149 606/41 |
| 2018/0147007 | A1* | 5/2018 | Purdy | A61B 18/082 |
| 2019/0053844 | A1* | 2/2019 | Hluchy | A61B 18/1445 |

* cited by examiner

*Primary Examiner* — Daniel W Fowler
(74) *Attorney, Agent, or Firm* — Fulwider Patton LLP

(57) ABSTRACT

A resectoscope having a curved sheath that can be made with different lengths, diameters and radii of curvature to better reach the areas of the bladder that are not accessible with a conventional resectoscope. The device is equipped with a fiber optic scope that follows the curved electrode tube and can transmit images for observing the interior of bladder where the surgical procedure is performed. The device of the present invention further comprises a modified obturator to facilitate the movement of the sheath inside the body, and interior guides on the sheath help move the cutting tool and obturator through the curved portions of the sheath.

6 Claims, 7 Drawing Sheets

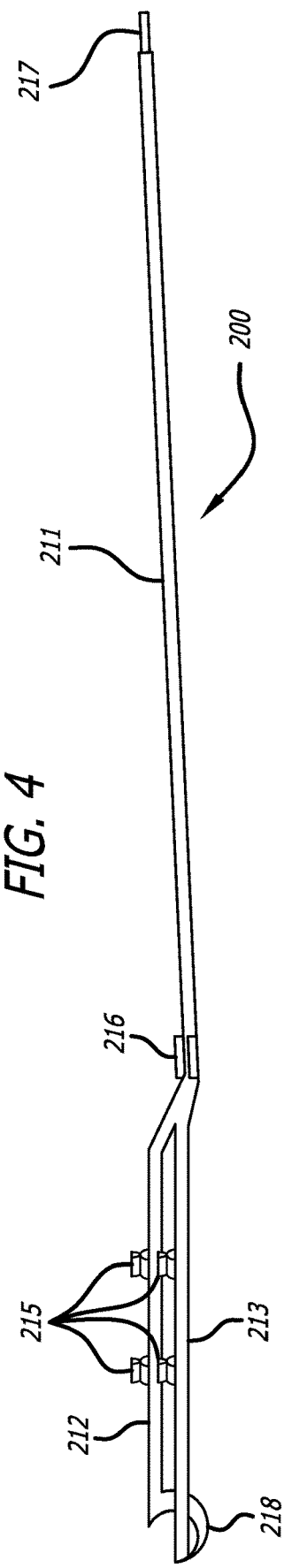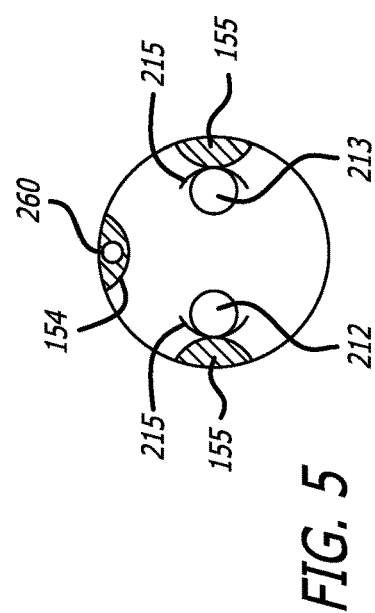

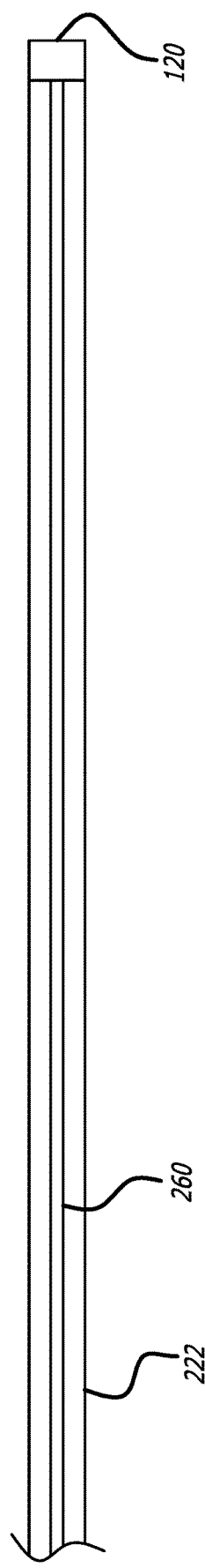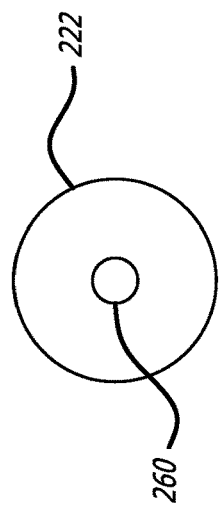

CURVED RESECTOSCOPE

CROSS-REFERENCES TO RELATED APPLICATIONS

This application claims priority to U.S. Provisional Patent Application No. 62/707,821, filed Nov. 20, 2017, the contents of which are fully incorporated herein by reference.

FIELD OF THE INVENTION

The present invention provides an improved resectoscope having electrode and telescope assemblies that reach areas of bladder that are difficult to access with the current resectoscopes.

BACKGROUND

A resectoscope is a medical device for resecting and removing tissue such as those found in the prostate and bladder. To remove a benign or cancerous tumor, for example, a piece of tissue is excised by repeated extensions and withdrawals of a heated wire loop.

The electrical current used to heat the wire loop can be provided by a monopolar or bipolar circuit. Monopolar circuits relies on an external grounding by attaching an electrode to the surface of the patient's body. The electrical current is directed from an external electrode to the active element and through the patient's body to the electrode that attached to the patient's body. In bipolar circuits, both the active and grounding electrodes are integrated and inserted together into the patient's body. The advantage of a bipolar circuit over a monopolar circuit is the electrical current path is not flowing through the patient's body, minimizing the obturator nerve reflex while the device is resecting the tumor in lateral wall of bladder.

Generally, a resectoscope apparatus comprises a cylindrical hollow sheath that is inserted in the body of the patient. The function of the sheath is to enclose and direct the resectoscope components such as the telescoping element, working element, and electrode assembly to the body. In addition, the sheath may include a secondary conduit that can be used for irrigation and/or drainage of bladder and surgical area.

One issue associated with the resectoscopes of the prior art is that they are linear to facilitate ingress into the body along a straight body channel such as the urethra, as shown in FIG. 1. When the linear shaft of the resectoscope is passed through the straight body channel and into the bladder, a substantial portion of the bladder's surface area is "hidden" from the resectoscope. That is, there is a portion of the bladder that inaccessible because the geometry of the resectoscope prevents the distal portion of the device to access the parabolic areas adjacent the entry point. These areas are thus left untreated, or more invasive procedures must be used to treat these areas. The present invention addresses this shortcoming of the prior art.

SUMMARY OF THE INVENTION

The present invention relates to a curved resectoscope that can be made with different lengths and diameters, and can reach the areas of the bladder that are not accessible with a regular straight resectoscope. The curvature is selected so that it is easy to pass through the urethra and prostate into the bladder. The distal end of the scope can be straight or slightly angled. In addition, the device is equipped with a fiber optic scope that follows the curved electrode tube and can transmit images for observing the interior of bladder where the surgical procedure is performed. The device of the present invention further comprises a modified obturator to facilitate insertion of the sheath inside the bladder. The present invention is applicable to both mono and bipolar circuits.

The device in a preferred embodiment includes an integrated groove or channel to provide guidance for the movement of cutting element assembly through the straight and curved areas of the sheath. Similarly, an additional groove or channel provides guidance for the fiber optic scope in the form of a wire and objective lens, through the tubular curved sheath. The groove or and channel also provide guidance for a obturator head.

BRIEF DESCRIPTION OF THE DRAWINGS

FIG. 4 is an elevated, perspective view of the cutting loop assembly of the present invention;
FIG. 5 is a cross sectional view of the sheath showing the cutting loop assembly arms secured to the ridges therein;
FIG. 7a is an elevated perspective view of an alternate embodiment where the ridge is replaced by a tube;
FIG. 7b is a cross sectional view of the embodiment of FIG. 9a taken along lines 10-10.

DETAILED DESCRIPTION OF THE PREFERRED EMBODIMENTS

Figure 1:
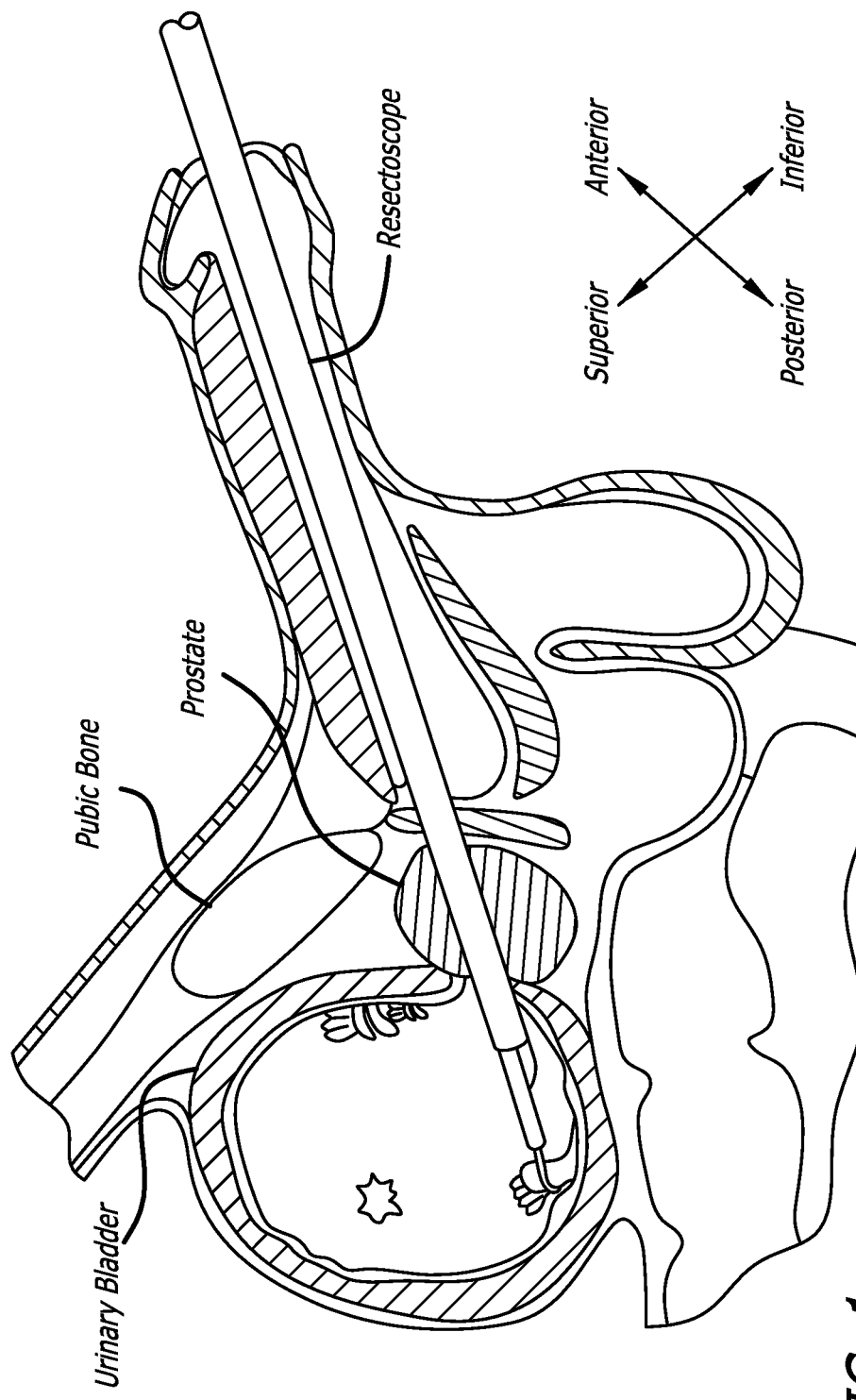
FIG. 1 is an illustration of a prior art resectoscope in use.
Figure 2:
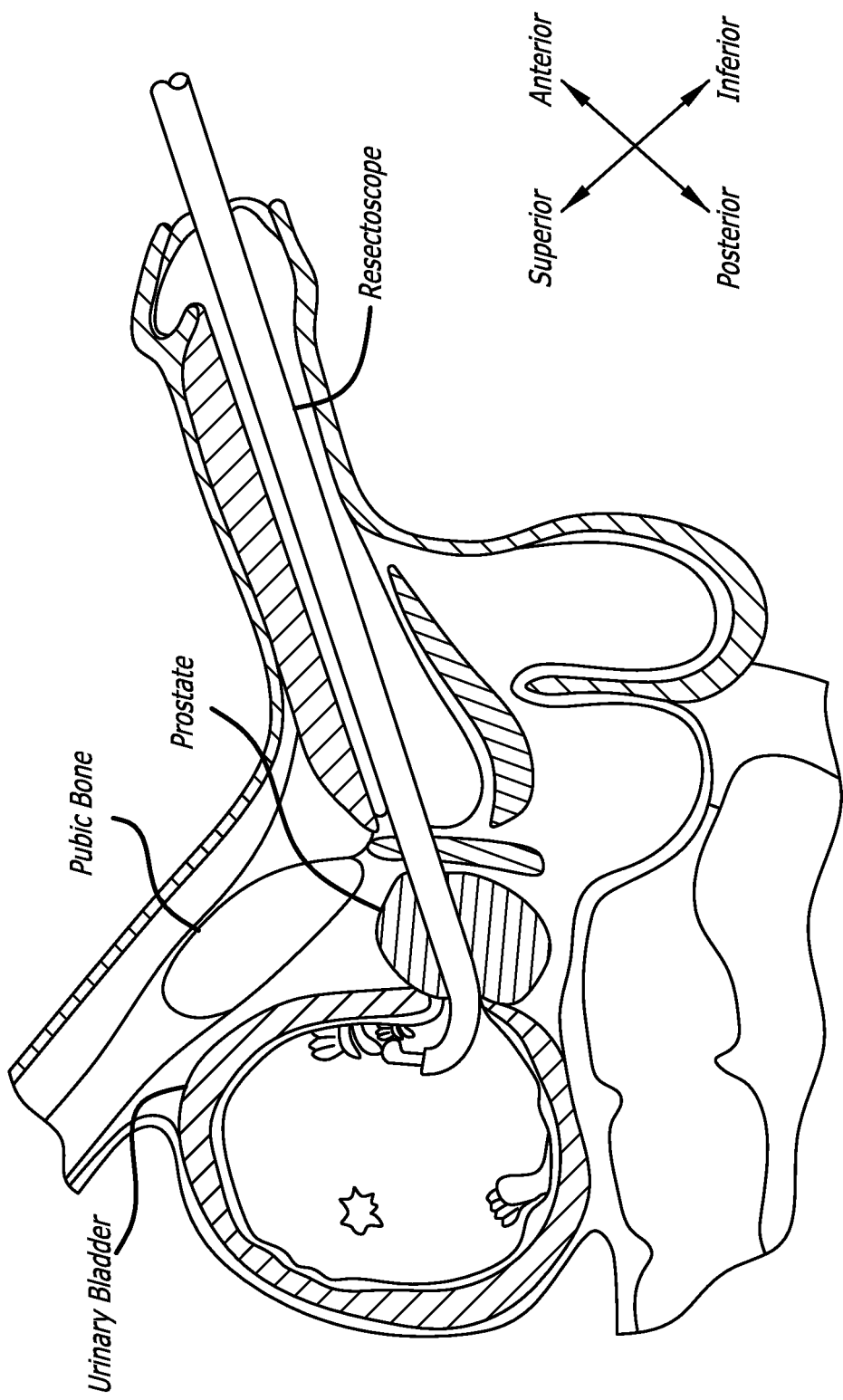
FIG. 2 is an illustration of the present invention in use.

The present invention is directed to an improved resectoscope that provides coverage for a wider afflicted area over existing devices. The operation of a prior art resectoscope is summarized in U.S. Pat. Nos. 7,169,147, and 6,730,084, the contents of which are both fully incorporated herein by reference, and thus the operation is not repeated herein for brevity. FIG. 2 illustrates an embodiment of the present invention in use. As compared with the scope of FIG. 1, it can readily be seen that the resectoscope of the present invention provides far more coverage and accessibility to affected areas of the bladder.

Figure 3A:
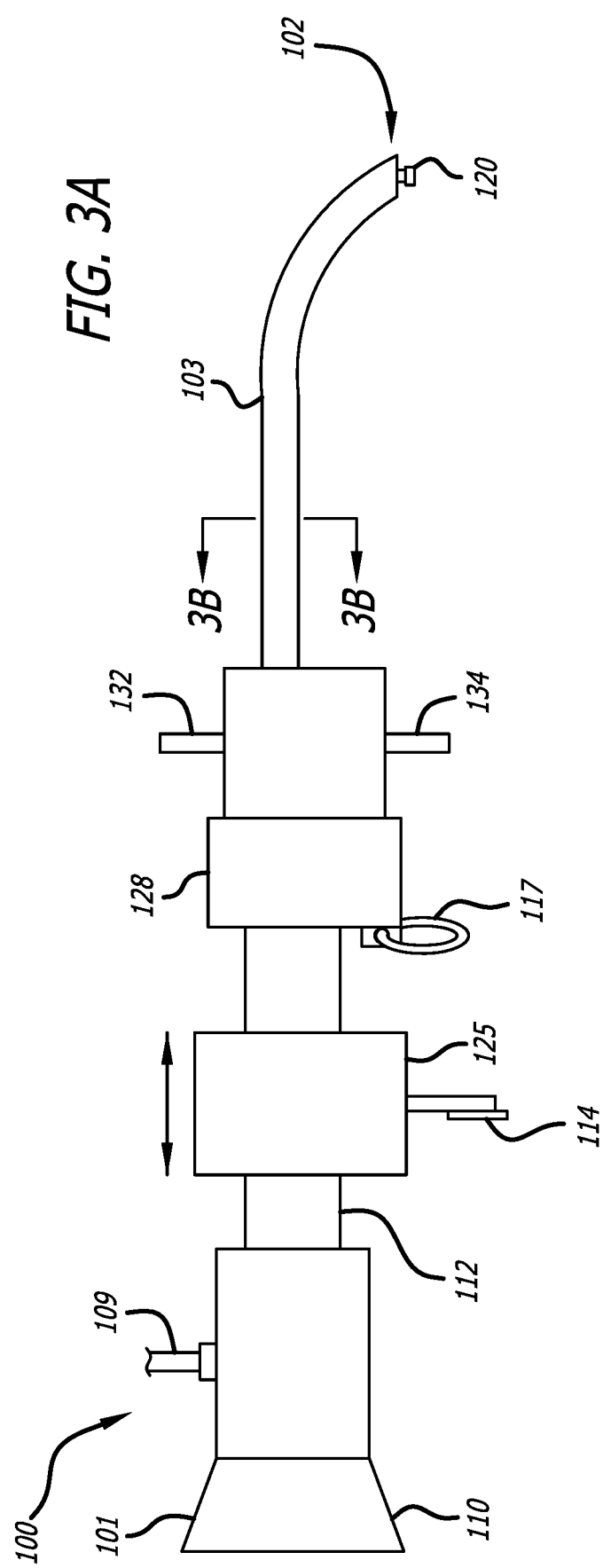
FIG. 3a is an elevated, perspective view of a first preferred embodiment of the present invention.

FIG. 3a illustrates various components of a first embodiment of the resectoscope 100 of the present invention, which includes a fiber optic assembly including an eyepiece 110 located at the proximal end, and an objective lens 120 at a distal end 102. A fiber optic cable coupling 109 is preferably located near the eyepiece 110 and connects to a fiber optic cable 260 that extends within a hollow guide rod 112 and into the sheath 103 through the length of the resectoscope to the lens 120. The resectoscope 100 can use the fiber optic coupling 109 to connect to a display for projecting the view at the distal portion of the device to a monitor, screen, or other display during the procedure or for recording the procedure.

Sliding block 125 is controlled by the operator using thumb pad 114 and finger ring 117 to move the sliding block 125 along the hollow guide rod 112 back and forth. Other devices for controlling the position of the sliding block 125, such as triggers, springs, cables, etc. are also known in the art. The main housing 128 includes a fluid port 132 for introducing irrigating fluid into the area of tissue resection and a vacuum port 134 for withdrawing fluid along with tissue, debris, blood, etc. In a modified version of the invention, to facilitate the plumbing system two co-axial sheaths are used. The inside sheath is the supply channel and the outer sheath which has a larger cross section is the suction channel. Alternatively, a single sheath can be employed that operates as both the supply and suction channels. Thus, the fluid port 132 can introduce fluid into a central lumen within an inner sheath (not shown) while the vacuum port can withdraw fluid and other matter in the annular recess between the inner sheath and the outer sheath 103. "Other arrangements can be made including providing an integral tube similar to 260 for the ingress and egress of irrigating fluids and materials to be removed.

Figure 3B:
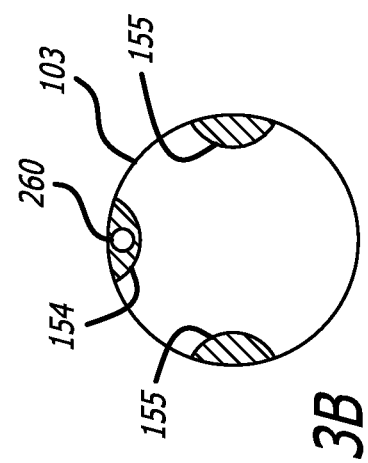
FIG. 3b is a cross sectional view of the sheath taken along lines 3b-3b.

FIG. 3b illustrates the inner periphery of the curved sheath 103 taken along a portion of the curved or straight section. The sheath 103 has along a first inner surface a first ridge 154 that includes a lumen for carrying the fiber optic cable 260 extending the length of the sheath 103. The first ridge 154 surrounds the cable 260 and allows the cable to bend and move with the sheath 103. The images passed from the objective lens 120 to the eye piece 110 or fiber optic coupling 109 assist the practitioner in guiding and moving the sheath through the body lumen. In addition, the inner surface of the lumen 103 includes a pair of diametrically opposed ridges 155 that are used to guide a cutting loop assembly as the cutting loop assembly moves down the sheath 103 along the straight and curved parts of the sheath.

FIG. 4 illustrates the cutting loop assembly 200, which comprises an elongate shank 211 having an electrical connector 217 at a proximal end. A power housing tube 216 surrounds a power element therein, which is used to energize the cutting loop 218. The shank 211 distally forks into first and second arms 212,213, and the arms 212 and 213 position the electrified cutting loop 218 at the distal end 102 of the device 100. Along the length of the arms 212, 213 are clips 215 that engage the ridges 155 of the sheath 103 to guide the cutting loop assembly 200 as it is pushed down the sheath 103. The clips 215 can be generally X shaped defining a curved upper channel and a curved lower channel, where one channel fit onto the respective arms 212, 213 while the other channel engages the ridge 155 inside the sheath 103. This configuration allows the cutting loop assembly 200 to be reliably maneuvered along the sheath, even along curved portions, to the distal end 102 for actuation.

Accordingly, as shown in FIG. 5, within the sheath 103 the first ridge 154 retains the fiber optic wire 260, and the diametrically opposed ridges 155 guide the movement of the arms 212, 213 of the cutting loop assembly 200 using clips 215 as the cutting loop assembly 200 moves along the sheath 103. Importantly, the sheath 103 includes both straight and curved portions. The diameter, the straight length, the curved length, and radius of curvature of the sheath can be varied to optimize the configuration for required application. The ridges 154, 155 can be continuous or intermittent along the length of the sheath 103, and the location of the ridges can be varied depending on the size of fork to facilitate the smooth movement of arms 212, 213 along the sheath. The cross section of the ridges can also be varied, and can be replaced by grooves, but it has been found that circular or elliptical cross sectional ridges work best. The ridges 154, 155 can either be an integral part of the sheath, or they can also be incorporated into a strip that is welded or mechanically attached to the sheath's inner surface.

Clips 215 are preferably flexible and may be made from a sturdy polymer material. If required, the diameter of the arms and shank can be decreased to increase the flexibility of this component. Cutting loop 218 can be maneuvered by the operator using the controls to extend out through sheath, and is heated by power supplied at the electrical connector 217. Movement of the cutting loop assembly 200 to cut the tissue using the cutting loop 218, the movement of which is controlled by the position of the sliding block 125.

Figure 6A:
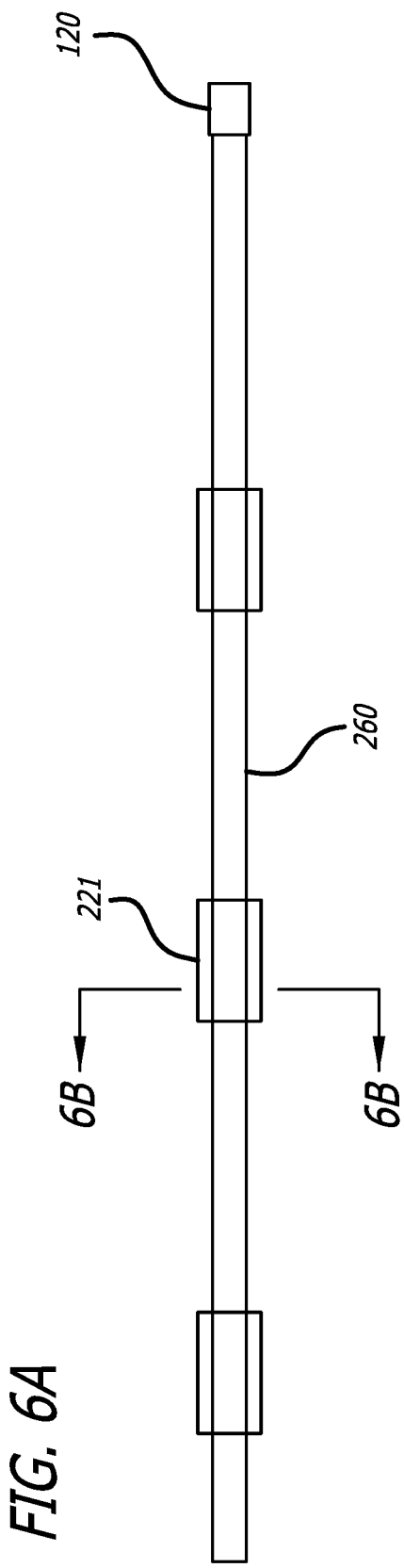
FIG. 6a is an elevated, perspective view of the fiber optics assembly.
Figure 6B:
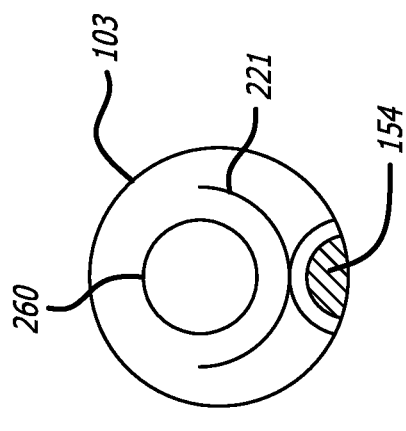
FIG. 6b is a cross sectional view of the fiber optics assembly taken along lines 6b-6b.

FIGS. 6a and 6b depict a portion of the fiber optics assembly in an alternate embodiment. In this embodiment, rather than having the optical fiber 260 be embedded in the ridge 154, the optical fiber is carried by a clip 221 in a manner similar to the arms of the cutting device described above. Here, optical fiber 260 extends along the length of the device 100, terminating at a lens 120. Along the length of the fiber 260 are clips 221, which operate in a similar manner to clips 215 in that projections from the clips 221 ride along ridge 154 within the sheath 103 to align and maneuver the optical fiber 260 along and through the sheath. Due to the flexibility of optical fiber 260, movement through the curved areas does not pose a problem. The lens 120 is centered at the exit point of sheath 103 to provide the greatest viewing angle of the U-shape cutting element 218 and cutting area. The centering of the lens 120 can be achieved by using a different clip size or a fixed locator attached to the sheath near the exit point. Another possibility is to have a thin tube 222 to house the fiber 260 as shown in FIGS. 7a and 7b. The tube material can be either a soft metal or a polymer. The tube 222 is suitably flexible and can follow the curved sheath using and clips 215 and ridge 154 as explained above. The tube 222 provides the required stiffness for the movement of the optical wire 260 as well as the tube itself. Due to the thin wall thickness, the tube 222 will be able to deflect through the curved area without buckling or crimping.

Figure 8:
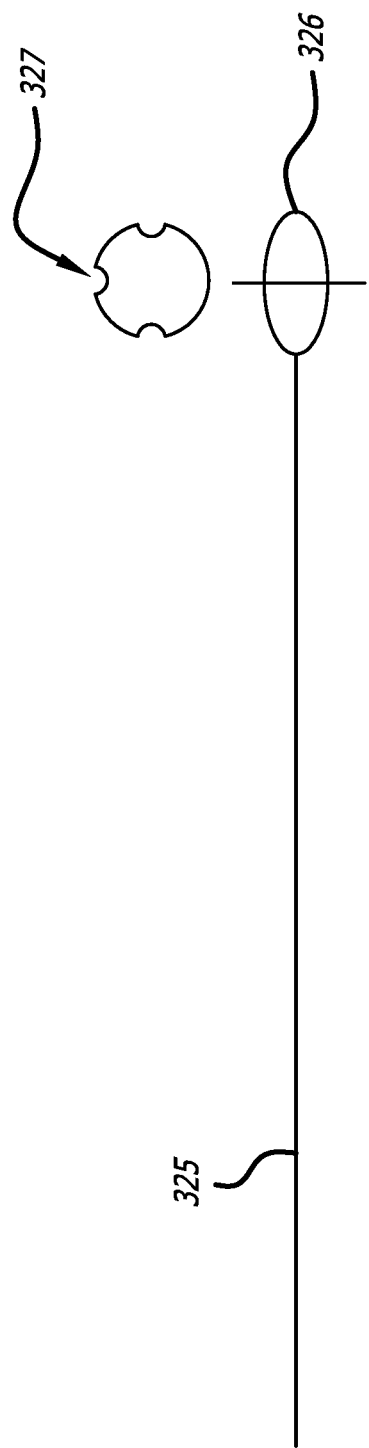
FIG. 8 is a schematic view of an obturator.
Figure 9:
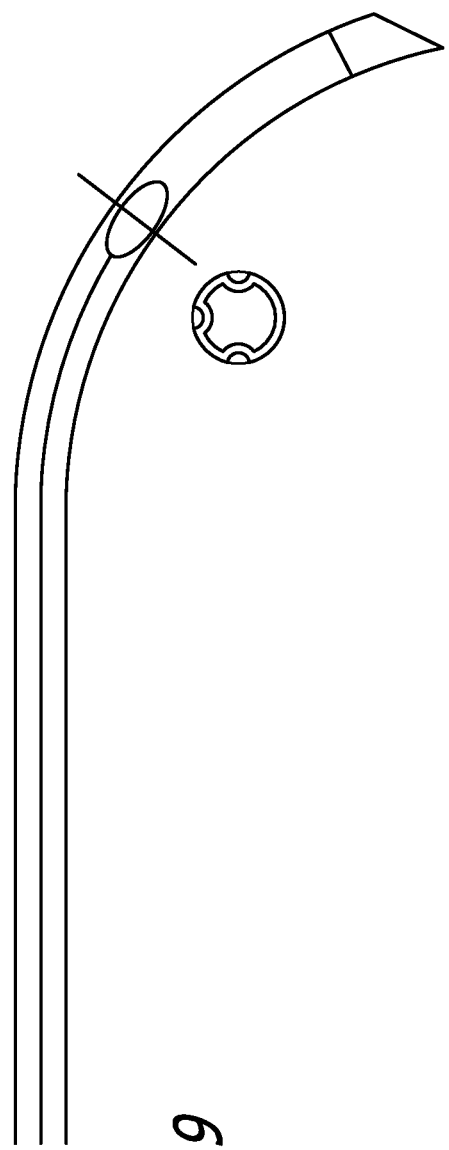
FIG. 9 is an enlarged, cross sectional view of the sheath and the obturator.

FIG. 8 illustrates an obturator 326 that may be used with the present invention. In a first embodiment, the traditionally stiff tube replaced with a flexible thin tube or rod 325. The flexibility of tube 325 is required to enable the movement in and through the curved portion of the sheath 103. The head of standard obturator is replaced by a small bullet shape configuration 326 with three aligned channels 327. The channels 327 are provided to help the smooth movement of obturator along the sheath without the interference from ridges 154, 155. FIG. 9 illustrates the position and movement of obturator 326 inside the sheath.

Additional advantages and modifications will readily occur to those skilled in the art. Therefore, the invention in its broader aspects is not limited to the specific details and representations depicted herein. That is, various modifications and substitutions that would be known to those skilled in the art are considered to be within the scope of the present invention, and the general inventive concept is represented by the appended claims and their equivalents.

We claim:
1. A resectoscope comprising:
an optical fiber assembly;
an irrigation port and channel from a main housing to a distal end;
an electrified cutting loop assembly;
a sliding block controlling a position of the electrified cutting loop assembly; and a sheath having a straight proximal section and a curved distal portion, the sheath comprising guides along an inner surface for guiding a movement of the electrified cutting loop assembly through the curved distal portion of the sheath;

wherein the guides comprise ridges longitudinally extending along an inner surface of the sheath, the electrified cutting loop assembly comprising clips that engage the ridges to position the electrified cutting loop assembly within the sheath; and wherein the electrified cutting loop assembly loop assembly includes two arms that connect to opposite sides of the sheath using said clips.

2. The resectoscope of claim 1, wherein the optical fiber assembly includes an optical cable at least partially embedded in a ridge formed on the inner surface of the sheath.

3. The resectoscope of claim 1, wherein the optical fiber assembly includes an optical cable that is enclosed in a flexible tube within the sheath.

4. The resectoscope of claim 1, wherein the optical fiber assembly includes an optical cable with a plurality of clips that engage a ridge on the inner surface of the sheath.

5. The resectoscope of claim 1, wherein the ridges are diametrically opposed and the clips are X shaped.

6. The resectoscope of claim 1, further comprising an obturator having longitudinal channels arranged to receive the ridges therein.

* * * * *